(12) United States Patent
Watanabe et al.

(10) Patent No.: US 8,580,235 B2
(45) Date of Patent: Nov. 12, 2013

(54) HAIR COSMETIC

(75) Inventors: Tomoko Watanabe, Yokohama (JP);
Tomoyuki Kawasoe, Yokohama (JP);
Takashi Teshigawara, Yokohama (JP);
Reiji Miyahara, Yokohama (JP);
Masatoshi Ochiai, Yokohama (JP);
Taizo Fujiyama, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 253 days.

(21) Appl. No.: 12/999,767

(22) PCT Filed: Jun. 19, 2009

(86) PCT No.: PCT/JP2009/061190
§ 371 (c)(1),
(2), (4) Date: Dec. 17, 2010

(87) PCT Pub. No.: WO2009/154269
PCT Pub. Date: Dec. 23, 2009

(65) Prior Publication Data
US 2011/0110877 A1 May 12, 2011

(30) Foreign Application Priority Data

Jun. 20, 2008 (JP) .................................. 2008-162424
Jul. 11, 2008 (JP) .................................. 2008-182088

(51) Int. Cl.
*A61K 8/49* (2006.01)
*A61K 8/86* (2006.01)
*A61K 31/704* (2006.01)
*A61Q 5/00* (2006.01)
*A61Q 5/02* (2006.01)

(52) U.S. Cl.
USPC .............. 424/59; 424/70.9; 424/401; 424/60; 514/547

(58) Field of Classification Search
USPC ........................ 424/59, 70.9, 401, 60; 514/547
See application file for complete search history.

(56) References Cited

U.S. PATENT DOCUMENTS

| | | | |
|---|---|---|---|
| 5,162,377 A * | 11/1992 | Kakoki et al. ................ | 514/772 |
| 6,017,556 A | 1/2000 | Luther et al. | |
| 6,495,122 B2 | 12/2002 | Fankhauser et al. | |
| 2004/0254129 A1* | 12/2004 | Soderlind ...................... | 514/35 |
| 2005/0008587 A1 | 1/2005 | Schulz et al. | |
| 2005/0129632 A1 | 6/2005 | Haase et al. | |
| 2007/0092459 A1 | 4/2007 | Bleckmann et al. | |

FOREIGN PATENT DOCUMENTS

| | | |
|---|---|---|
| EP | 1779839 A1 | 5/2007 |
| EP | 2305207 | 4/2011 |
| JP | 55-098109 * | 7/1980 |
| JP | 7-33628 A | 2/1995 |
| JP | 2003-40740 A | 2/2003 |
| JP | 2006-111620 * | 4/2006 |
| JP | 2006-327952 * | 7/2006 |
| JP | 2007-8867 A | 1/2007 |
| JP | 2007070232 A | 3/2007 |
| JP | 2008-137966 A | 6/2008 |

OTHER PUBLICATIONS

International Preliminary Report issued in counterpart PCT Application No. PCT/JP2009/061190.
Supplementary European Search Report issued on Jul. 5, 2011, in counterpart European Patent Application No. 09766717.
International Search Report issued in corresponding PCT/JP2009/061190.
Notification of the First Office Action issued on Aug. 24, 2011 in corresponding Chinese Application No. 200980116532.9, with a partial English Translation thereof.
Taiwanese Pat. Appln. S.N. 098120700, Office Action dated Jul. 12, 2012, 4 pgs.—Chinese, 2 pgs.—English.
Chinese Pat. Appln. Serial No. 200980116532.9, $2^{nd}$ Office Action dated Jul. 23, 2012, 4 pgs.—English, 3 pgs.—Chinese.
Korean Pat. Appln. Serial No. 10-2010-7026508 dated Feb. 14, 2011, 3 pgs.—English, 4 pgs.—Korean.
Handbook of Cosmetic Ingredients, $5^{th}$ Edition, Fragrance Journal, Ltd., Jul. 25, 2005, 3 pages—English, 3 pages—Japanese.
Manufacturing Technology of Cosmetics, Fragrance Journal Ltd., $1^{st}$ Edition, Aug. 25, 2001, 4 pages—English, 6 pages—Japanese.

* cited by examiner

*Primary Examiner* — Fereydoun G Sajjadi
*Assistant Examiner* — Ana Falkowitz
(74) *Attorney, Agent, or Firm* — Andrew F. Young, Esq.; Lackenbach Siegel, LLP

(57) ABSTRACT

An object of the present invention is to establish means for reliably incorporating a poorly soluble UV-absorbing agent into a hair cosmetic composition, to thereby provide a hair cosmetic composition which has excellent effect of preventing UV-hair damage and which exhibits favorable sensation in use thereof. Specifically, the object can be attained through provision of a hair cosmetic composition including the following ingredients (1) and (2):

(1) a polyoxy(lower alkylene) addition compound represented by formula (I):

[F1]

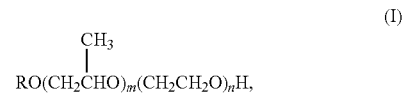

wherein R represents a phytosterol residue or a phytostanol residue; m is a number from 0 to 100; and n is a number from 5 to 100, and (2) a UV-absorbing agent having a triazine group.

24 Claims, No Drawings

HAIR COSMETIC

TECHNICAL FIELD

The present invention relates to a hair cosmetic composition, and more particularly, to a hair cosmetic composition containing a UV-absorbing agent having a triazine group which exhibits excellent UV-shielding effect but has poor solubility. The cosmetic composition provides favorable sensation in use and can be employed in shampooing and styling.

BACKGROUND ART

It is empirically known that the hair is damaged by UV-rays. In recent years, there has been particular concern about the adverse effects of UV-rays included in sunlight. The applicant previously elucidated that when the hair is exposed to UV-rays, protein that forms the hair is oxidized, and elution of the oxidized protein is promoted, which contributes to hollowing of hair and poor sensation to the touch (e.g., overly dry sensation or rough sensation). Some studies have revealed that the hair protein is oxidized even through exposure to UV rays for a very short period of time, and, in addition, both UVA and UVB can cause the oxidation.

SUMMARY OF THE INVENTION

Problems to be Solved by the Invention

As described above, incorporation of a UV-absorbing agent into a hair cosmetic composition is effective means for preventing hair damage caused by exposure to UV rays such as those found in sunlight. However, the types of UV-absorbing agents which can protect the hair from UVA (long wavelength UV-ray) are limited in number, and most of such UV-absorbing agents have low solubility. Therefore, in order to prevent hair damage through incorporation of a poorly soluble UV-absorbing agent into a hair cosmetic composition, large amounts of additives such as a surfactant must be used. As a result, the produced hair cosmetic composition exhibits poor sensation in use, which is problematic. Thus, an object attained by the present invention is to establish means for reliably incorporating a poorly soluble UV-absorbing agent into a hair cosmetic composition, to thereby provide a hair cosmetic composition which has excellent effect of preventing UV-hair damage and which exhibits favorable sensation in use thereof.

Means for Solving the Problems

The present inventors have conducted extensive studies on UV-absorbing agents having a triazine group, which generally exhibit excellent UVA absorption effect but have a low solubility, and have found that co-presence of a UV-absorbing agent having a triazine group with a surfactant having a phytosterol skeleton or a phytostanol skeleton as a hydrophobic molecule and a polyoxyethylene chain (POE chain), or a polyoxyethylene chain (POE chain)-polyoxypropylene chain (POP chain) block chain (hereinafter may be referred to as a POE-POP block chain) as a hydrophilic molecule, realizes protection of the hair from UV oxidation damage and excellent sensation in use thereof.

Accordingly, the present invention provides a hair cosmetic composition comprising the following ingredients (1) and (2) (hereinafter may be referred to as hair cosmetic composition of the present invention):

(1) a polyoxy(lower alkylene) addition compound represented by formula (I) (hereinafter may be referred to as compound (I)):

[F1]

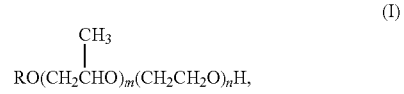

wherein R represents a phytosterol residue or a phytostanol residue; m is a number from 0 to 100; and n is a number from 5 to 100, and (2) a UV-absorbing agent having a triazine group (hereinafter may be referred to as triazine UV-absorbing agent).

Examples of the form of hair cosmetic compositions to which the present invention can be applied include hair washing materials such as shampoo, rinse, rinse-in-shampoo, and a hair conditioner; and hair-treatment agents such as hair foam, hair mousse (registered trademark), hair spray, hair mist, hair gel, setting lotion, curler lotion, hair liquid, hair wax, hair treatment (hair cream, hair blow, etc.), a hair nutrient, a hair coloring agent, a permanent waving agent, and a curly-hair-straightening agent. As used herein, the term "hair-treatment agent" represents a "hair-treatment composition."

Effects of the Invention

According to the present invention, there is provided a hair cosmetic composition which can effectively suppress hair damage which would otherwise be caused by UV rays and which exhibits favorable sensation in use thereof.

MODES FOR CARRYING OUT THE INVENTION

Incorporation of Polyoxy(Lower Alkylene) Addition Compound (Compound (I))

As mentioned above, the hair cosmetic composition of the present invention contains a poorly water-soluble triazine UV-absorbing agent and compound (I). As described hereinbelow, compound (I) incorporated into the hair cosmetic composition of the present invention may be a single compound among the compounds represented by formula (I), or a mixture of two or more different compounds.

No particular limitation is imposed on the phytosterol, which is a compound that provides a phytosterol residue represented by R in compound (I), and is a plant-derived sterol (F. D. Gunstone and B. G. Herslof, A Lipid Glossary, The Oily Press, Air, 1992). Examples of the phytosterol residue represented by R include a sitosterol residue, a campesterol residue, a stigmasterol residue, a brassicasterol residue, an avenasterol residue, and an ergosterol residue. As described above, compound (I) contained in the water-containing composition of the present invention may be a mixture of two or more compounds having different phytosterol residues represented by R.

Similarly, no particular limitation is imposed on the phytostanol, which is a compound that provides a phytostanol residue represented by R in compound (I), and is obtained through hydrogenation (or saturation) of the corresponding phytosterol. Examples of the phytostanol residue represented by R include sitostanol, campestanol, stigmastanol, brassicastanol, avenastanol, and ergostanol. As described above, compound (I) contained in the hair cosmetic composition of the present invention may be a mixture of two or more compounds having different phytostanol residues represented by R.

Compound (I) contained in the hair cosmetic composition of the present invention may be a mixture of one compound having a phytosterol residue represented by R, or two or more compounds having different phytosterol residues, and one compound having a phytostanol residue represented by R, or two or more compounds having different phytostanol residues.

In compound (I), the number (m) of polyoxypropylene chains (POP chains), is 0 to 100, preferably 0, or 5 to 50. The number (n) of polyoxyethylene chains (POE chains) is 5 to 100, preferably 10 to 50. That is, compound (I) is a polyoxy (lower alkylene) addition compound in which the polyoxy (lower alkylene) chain is a POE chain or a block chain of a POP chain and a POE chain.

The amount of compound (I) incorporated into the hair cosmetic composition of the present invention is preferably 0.01 to 10 mass % with respect to the composition, more preferably 0.1 to 5 mass %. When the amount is less than 0.01 mass, difficulty is encountered in dispersion or solubilization of the triazine UV-absorbing agent to such a degree that substantial UV-shielding effect can be attained, whereas when the amount is in excess of 10 mass %, the produced cosmetic composition is liable to have stickiness. In addition, the amount of compound (I) greatly depends on the relationship between the amount thereof and that of triazine UV-absorbing agent incorporated into the composition. The ratio by mass of compound (I) to triazine UV-absorbing agent in the composition is preferably 1 or higher, particularly preferably 3 or higher (the upper limit of this ratio is determined on the basis of the upper limit of the amount of compound (I)). A suitable lower limit of the amount of compound (I) may be determined on the basis of this ratio by mass.

[Incorporation of Triazine UV-Absorbing Agent]

The hair cosmetic composition of the present invention must contain one or more triazine UV-absorbing agents; i.e., UV-absorbing agents having a triazine group. Although the triazine UV-absorbing agent is poorly water-soluble, no particular limitation is imposed on the solubility in a solvent other than water. So long as the triazine UV-absorbing agent is contained in the composition, another poorly water-soluble UV-absorbing agent or a water-soluble UV-absorbing agent may also be incorporated into the composition.

Examples of the triazine UV-absorbing agent include bis-resorcinyltriazine, more specifically, bisethylhexyloxyphenol methoxyphenyltriazine (2,4-bis{[4-(2-ethylhexyloxy)-2-hydroxy]phenyl}-6-(4-methoxyphenyl)-1,3,5-triazine), TINOSORB S (commercial product of Ciba Specialty Chemicals), octyl triazone (2,4,6-tris[4-(2-ethylhexyloxycarbonyl)anilino]-1,3,5-triazine), 2,4,6-trianilino-p-(carbo-2'-ethylhexyl-1'-oxy)-1,3,5-triazine, UVINUL T150 (commercial product of BASF), 2-[2-hydroxy-4-(2-ethylhexyl)phenoxy]-2H-benzotriazole, and dioctylbutamidotriazone (Uvasorb HEB, commercial product of 3V sigma).

The amount of the triazine UV-absorbing agent incorporated into the hair cosmetic composition of the present invention is preferably adjusted in accordance with the aforementioned ratio of amount of compound (I) to amount of triazine UV-absorbing agent (I). Generally, the amount of the triazine UV-absorbing agent is preferably 0.001 to 3 mass % with respect to the cosmetic composition, more preferably 0.001 to 1 mass %. When the amount is less than 0.001 mass, the hair cosmetic composition of the present invention encounters difficulty in substantial suppression of hair damage based on the UV-shielding action, whereas when the amount is in excess of 3 mass %, the amount exceeds the upper limit of practical solubility of the triazine UV-absorbing agent.

As described above, the hair cosmetic composition of the present invention does not exclude incorporation of another UV-absorbing agent other than the triazine UV-absorbing agent. Examples of such UV-absorbing agent include benzoic acid UV-absorbing agents (e.g., p-aminobenzoic acid (hereinafter abbreviated as "PABA"), PABA monoglycerin ester, N,N-dipropoxy-PABA ethyl ester, N,N-diethoxy-PABA ethyl ester, N,N-dimethyl-PABA ethyl ester, N,N-dimethyl-PABA butyl ester, and N,N-dimethyl-PABA ethyl ester); anthranilic acid UV-absorbing agents (e.g., homomethyl-N-acetyl anthranilate); salicylic acid UV-absorbing agents (e.g., amyl salicylate, menthyl salicylate, homomethyl salicylate, octyl salicylate, phenyl salicylate, benzyl salicylate, and p-isopropanolphenyl salicylate); cinnamic acid UV-absorbing agents (e.g., octyl cinnamate, ethyl 4-isopropylcinnamate, ethyl 2,4-diisopropylcinnamate, methyl 2,4-diisopropylcinnamate, propyl p-methoxycinnamate, isopropyl p-methoxycinnamate, cyclohexyl p-methoxycinnamate, ethyl α-cyano-β-phenylcinnamate, and 2-ethylhexyl α-cyano-β-phenylcinnamate); benzophenone UV-absorbing agents (e.g., 2-[4-(diethylamino)-2-hydroxybenzoyl]benzoic acid hexyl ester, 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salt, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzylidene)-d,l-camphor and 3-benzylidene-d,l-camphor; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenyl)benzotriazole; dibenzaladine; dianisoylmethane; 4-methoxy-4'-t-butyldibenzoylmethane; and 5-(3,3-dimethyl-2-norbornylidene)-3-pentan-2-one; phenyl acrylate UV-absorbing agents (e.g., 2-ethylhexyl-2-cyano-3,3-diphenyl acrylate and 2-ethyl-2-cyano-3,3-diphenyl acrylate); phenylbenzimidazole derivatives (e.g., phenylbenzimidazole sulfonic acid and disodium phenyl dibenzimidazole tetrasulfonate); dibenzoylmethane UV-absorbing agents (e.g., 4-tert-butyl-4'-methoxydibenzoylmethane); camphor derivatives (e.g., 4-methylbenzylidene camphor and terephthalylidene dicamphor sulfonic acid); phenylbenzotriazole derivatives (e.g., hydroxy-(ethylhexyl)phenoxybenzotriazole and methylenebis-benzotriazolyltetramethylbutylphenol); and benzalmalonate derivatives (e.g., dimethico benzalmalonate).

These additional UV-absorbing agents may be incorporated into the cosmetic composition, regardless of the water-soluble or poorly water-soluble nature. No particular limitation is imposed on the amount(s) of the additional UV-absorbing agents, so long as the effects of the present invention are not impeded.

[Incorporation of Water]

The hair cosmetic composition of the present invention may be mixed with water, to thereby provide a water-containing composition, i.e., an aqueous hair cosmetic composition. In this case, the water incorporated into the hair cosmetic composition of the present invention is generally ion-exchanged water, purified water, or tap water. The amount of water incorporated into the hair cosmetic composition of the present invention may be the balance (excepting compound (I) and triazine UV-absorbing agent) of the cosmetic composition, or the balance (excepting compound (I), triazine UV-absorbing agent, and other general ingredients) of the cosmetic composition.

In the water-containing hair cosmetic composition of the present invention, through co-presence of compound (I), which is a surfactant having a phytosterol skeleton or a phytostanol skeleton as a hydrophobic molecule and a POE chain, or a POE chain-POP chain as a hydrophilic molecule, and a UV-absorbing agent having a triazine group in the aqueous system, the surfactant is effectively dispersed or solubilized in water, thereby realizing a stable mixing state.

SPECIFIC EMBODIMENTS OF THE PRESENT INVENTION

The hair cosmetic composition of the present invention may be applicable to water-free compositions such as hair spray and hair oil; and water-containing compositions such as shampoo, a conditioner, hair wax, a hair treatment agent, and hair cream.

The water-free composition can be produced through mixing portions which form the composition. In the case of the water-containing composition, the production method therefor varies depending on the form of the target hair cosmetic composition. However, in one typical production method, at least a triazine UV-absorbing agent is dissolved or dispersed in compound (I), to thereby prepare an oil phase portion. The oil phase portion is added to an aqueous phase portion, to thereby solubilize or disperse the oily ingredient(s).

As described above, the hair cosmetic composition of the present invention is typically employed as (1) a hair-washing agent or (2) a hair-treatment agent. The hair cosmetic composition of the present invention may be formed into a hair cosmetic composition of interest by incorporating optional ingredients which are generally employed in the art and required for the selected form into the composition, through, for example, the aforementioned procedure.

No particular limitation is imposed on the general ingredient, although the examples thereof will be given. In addition, embodiments of the hair cosmetic composition of the present invention which may contain a general ingredient will be described as the forms of hair-washing agent and hair-treatment agent.

Specific examples of the anionic surfactant include alkylsulfuric acid salts, alkyl ether sulfuric acid salts, higher fatty acid salts, alkylsulfonic acid salts, POE alkylsulfuric acid salts, alkylbenzenesulfonic acid salts, N-acylsarcosine salts, N-acylisethionic acid salts, N-acylglutamic acid salts, α-olefinsulfonic acid salts, alkyl ether acetic acid salts, and POE alkyl ether acetic acid salts.

Specific examples of the cationic surfactant include alkyltrimethylammonium salts, dialkyldimethylammonium salts, alkyldimethylbenzylammonium salts, alkylisoquinolinium salts, dialkylmorpholinium salts, POE alkyl amines, alkylamine salts, polyamine fatty acid derivatives, amyl alcohol fatty acid derivatives, benzalkonium chloride, and benzethonium chloride.

Specific examples of the nonionic surfactant include alkanolamides, glycerin fatty acid esters, polyoxyalkylene alkyl ethers, polyoxyalkylene glycols, polyoxyalkylene sorbitan fatty acid esters, sorbitan fatty acid esters, polyoxyalkylene sorbitol fatty acid ester, sorbitol fatty acid ester, polyoxyalkylene glycerin fatty acid esters, polyoxyalkylene fatty acid esters, polyoxyalkylene alkylphenyl ethers, tetrapolyoxyalkylene-ethylenediamine condensates, polyoxyalkylene ethers, sucrose fatty acid esters, polyoxyalkylene fatty acid amides, polyoxyalkylene glycol fatty acid esters, polyoxyalkylene castor oil derivatives, polyoxyalkylene hardened castor oil derivatives, and alkyl polyglycosides.

Specific examples of the ampholytic surfactant include alkylimidazolinium betaines, alkylamidopropyl betaines, alkylaminocarboxylic acids, alkylsulfobetaines, alkylamine oxides, alkylcarboxybetaines, and alkylbetaines.

Specific examples of the oily ingredient include olive oil, jojoba oil, castor oil, lanolin, beeswax, carnauba wax, liquid paraffin, squalane, microcrystalline wax, stearic acid, isostearic acid, oleic acid, cetanol, stearyl alcohol, cetyl octanoate, isopropyl myristate, dimethylpolysiloxane, methylphenylpolysiloxane, silicone reins, silicone rubber, amino-modified polysiloxane, and polyether-modified polysiloxane.

Specific examples of the humectant include polyethylene glycol, glycerin, 1,3-butanediol, 1,2-pentanediol, erythritol, sorbitol, xylitol, maltitol, propylene glycol, dipropylene glycol, diglycerin, sodium pyrrolidonecarboxylate, lactic acid, and sodium lactate.

Specific examples of the polymeric viscosity-adjusting agent include methylcellulose, hydroxyethylcellulose, and carboxymethylcellulose.

(1) Hair-Washing Agent

In the case where the hair-washing agent is a shampoo, the aforementioned anionic surfactant may be employed as a foaming agent. In addition, the aforementioned ampholytic surfactant or nonionic surfactant may be added to the shampoo. Examples of the general ingredient employed in the shampoo include an oily ingredient, a cationic polymer such as cationized cellulose (conditioning agent), the aforementioned humectants, a thickener, the aforementioned viscosity-adjusting agents, a pH-adjusting agent, an emulsifying agent, a dye, a sequestering agent, and a preservative. In order to prevent dandruff and itches, there may be incorporated, into the shampoo, trichlorocarbanilide, sulfur, salicylic acid, zinc pyrithione, isopropylmethylphenol, etc.

When the hair-washing agent is a rinse or hair conditioner (hereinafter collectively referred to as rinse or the like), the aforementioned cationic surfactant, and optionally the aforementioned oily ingredient, humectant, etc. may be incorporated thereinto. The hair cosmetic composition of the present invention may be a clear rinse or the like in which an oily ingredient is dissolved in aqueous solution of a cationic surfactant, or an emulsion-type rinse or the like which is formed of a gel having a layered structure consisting of a cationic surfactant, a higher alcohol, and water.

When the hair-washing agent is a rinse-in-shampoo, one possible embodiment contains the aforementioned anionic surfactant as a main washing agent, the aforementioned cationic surfactant or silicone as a conditioning agent, a hydrocarbon oily ingredient, etc.

(2) Hair-Treatment Agent

In the case where a hair foam or hair mousse (registered trademark) is employed as a finishing hair cosmetic composition, the composition of the present invention as is (neat liquid) is employed. The neat liquid may contain generally employed ingredients. Examples thereof include a setting agent such as a nonionic polymer (e.g., polyvinylpyrrolidone or polyvinylpyrrolidone/vinyl acetate copolymer), an anionic polymer (e.g., acrylic acid ester/methacrylic acid ester copolymer or vinyl methyl ether/butyl maleate copolymer), a cationic polymer (e.g., vinylpyrrolidone/dimethylaminoethyl methacrylate copolymer cationized products), or an ampholytic polymer (e.g., hydroxypropyl acrylate/butylaminoethyl methacrylate/octylamide acrylate copolymer); the aforementioned oily ingredients and humectants, and surfactants generally employed for emulsification.

When the hair-treatment agent is a hair spray or a hair mist, similar to the aforementioned hair foam or the like, the composition of the present invention as is (neat liquid) may be employed. Examples of main ingredients which may be incorporated into the hair spray include a film-forming agent such as polyvinylpyrrolidone or a vinyl acetate copolymer thereof; acrylic resin alkanolamine liquid, or vinyl methyl ether/butyl maleate copolymer; a higher alcohol such as cetyl alcohol, stearyl alcohol, isostearyl alcohol, or cetanol; solid oily ingredients such as a lanolin derivative; and silicone oil.

When the hair-treatment agent is a hair gel, an aqueous polymer (e.g., carboxyvinyl polymer, methylcellulose, or carrageenan) is employed for forming a viscous system. In addition, the aforementioned setting agent and humectant, and an alkali agent, a surfactant generally employed for emulsification, a sequestering agent, etc. may be incorporated into the hair gel.

When the hair-treatment agent is a setting lotion or a curler lotion, the lotion may further contain, for example, the aforementioned setting agent and humectant, and a plasticizer.

When the hair-treatment agent is a hair liquid, the hair liquid may further contain, for example, polyalkylene glycol as a styling agent.

When the hair-treatment agent is a hair wax, the hair wax may further contain a solid oily ingredient (a wax such as candelilla wax, carnauba wax, or beeswax; a hydrocarbon oil such as liquid paraffin, petrolatum, ceresin, or microcrystalline wax; a higher fatty acid such as lauric acid or myristic acid; or the aforementioned higher alcohol); a liquid oily ingredient; a semi-solid oily ingredient; the aforementioned thickener; the aforementioned humectant; and a surfactant generally employed for emulsification.

When the hair-treatment agent is a hair cream, the hair cream may further contain fats and oils such as olive oil, camellia oil, and synthetic triglyceride; the aforementioned hydrocarbon oil, wax, and higher fatty acid; higher fatty acid esters such as isopropyl myristate and butyl stearate; the aforementioned higher alcohol and thickener; and an organic amine or inorganic alkali, a preservative, and a sequestering agent.

When the hair-treatment agent is a hair blow, the aforementioned cationic surfactant, ethanol, a silicone derivative, the aforementioned humectant, the aforementioned oily ingredients, a protein hydrolysate, and a preservative may be incorporated thereinto.

EXAMPLES

The present invention will next be described in detail by way of examples, which should not be construed as limiting the invention thereto. Unless otherwise specified, the amount of a component is based on mass % with respect to the object into which the component is incorporated. The working examples of the hair cosmetic composition of the present invention include Examples A (hair-washing agents) and Examples B (hair-treatment agents). In each of Examples A and B, compound (I) having a POE chain as a hydrophilic molecule, and compound (I) having a POE-POP block chain as a hydrophilic molecule were tested.

1. Testing Procedures (1) Assessing UV-Shielding Effect

Keratin film prepared from protein extracted from the hair was employed. Each sample was applied to keratin film, and the UV-shielding effect of the sample was measured.

(Preparation of Keratin Film)

A hair sample (600 mg) obtained from a 15-year-old female was immersed in a liquid mixture containing urea (30 mass %), thiourea (20 mass %), dithiothreitol (5 mass %), and 25 mM Tris-HCl buffer (pH: 8.5) (8 mL), to thereby prepare a hair sample solution. The solution was incubated at 50° C. for four days, to thereby prepare a hair keratin protein solution. Unextracted hair residues were removed from the solution through filtration, to thereby prepare a hair protein solution. To the protein solution (3.5 mg), 100 mM aqueous acetic acid solution (6 mL) was added, and the thus-obtained mixture solution was gently cast into a petri dish (diameter: 35 mm) filled with water. The solution was solidified and brought into contact several times with a development solution containing distilled water, whereby the solution in the gel was substituted by distilled water. Finally, distilled water was removed from the cast gel, and the dried cast gel was sufficiently dried in a box including silica gel therein, to thereby produce a target keratin film.

Through the following experiment procedure employing the thus-produced keratin film, increase in fluorescence intensity was measured.

(Measurement of Increase in Fluorescence Intensity)

(a) Application Sample to Keratin Film

In Examples (A) (hair-washing agents), each of the samples (Examples and Comparative Examples) is 4-fold diluted with distilled water, and the diluted sample (3 g) is poured to the petri dish in which the keratin film is placed. The contents of the petri dish are shaken for three minutes (with foaming in the case of shampoo). Thereafter, the sample is removed, and the keratin film is washed 7 times with distilled water (1.5 mL each) and dried.

In Examples (B) (hair-treatment agents), there is provided a quartz glass plate ($\phi$: 34 mm, no UV absorption, thickness: 1 mm) whose dimensions are fitted to a petri dish including a keratin film therein. Each (1 mL) of the samples (Examples and Comparative Examples) is applied onto the quartz glass plate, and dried at 50° C. for 24 hours. Aluminum foil is placed on the half area of the keratin film so as to be unirradiated, and the quartz glass plate treated with the sample is placed on the keratin film.

(b) Irradiation of Keratin Film with UV Rays

In Examples (A) (hair-washing agents), the keratin film is irradiated with artificial sun light by a solar simulator (15 mW/cm$^2$, 290 to 390 nm) for 10 minutes. During irradiation, the half area of the film is shielded with aluminum foil so as to be unirradiated. The procedure from treatment with the sample to irradiation with artificial sun light by a solar simulator is repeated seven times.

In Examples (B) (hair-treatment agents), the keratin film is irradiated with artificial sun light by a solar simulator (15 mW/cm$^2$, 290 to 390 nm) for one hour (54 J/cm$^2$).

(c) Staining the Keratin Film After UV Irradiation

5-FTSC is dissolved in dimethyl sulfoxide, to thereby prepare a 5 mM 5-FTSC solution. The thus-prepared 5 mM 5-FTSC solution is dissolved in 0.1M MES (2-morpholinoethanesulfonic acid monohydrate) whose pH has been adjusted with sodium hydroxide to 5.5, whereby a 20 μM 5-FTSC/0.1M MES-Na (pH: 5.5) staining solution is prepared. In a specific staining procedure, the 20 μM 5-FTSC/0.1M MES-Na (pH: 5.5) staining solution is poured to a petri dish including the keratin film therein, and the dish are shaken at room temperature for 15 minutes. After completion of sufficient staining, the keratin film is washed so as to remove the staining solution. Specifically, the solution remaining after shaking is removed from the petri dish, and 2×SSC-0.1% SDS solution is poured to the dish, followed by shaking at room temperature for five minutes. Then, the washing solution is renewed, and the above washing procedure is repeated. Subsequently, 0.2×SSC-0.1% SDS solution is poured to the dish, and the dish is incubated at 50° C. for 20 minutes. The washing solution is replaced, and the washing procedure is repeated. Thereafter, distilled water is poured to the dish, and the dish is shaken at room temperature for two minutes. The distilled water is renewed, and the washing procedure with distilled water is repeated six times in total. All the steps of preparing the staining solution, staining, and washing are performed in the dark.

(d) After completion of staining the washed keratin film in a desiccator, each keratin film is observed by using a fluorescence microscope, and the fluorescent images of the unirradiated area and the irradiated area are taken. The fluorescence intensity of each area is measured. The value obtained by subtracting the fluorescence intensity of the unirradiated area from that of the irradiated area is defined as the increase in fluorescence intensity. The smaller the increase in fluorescence intensity, the more excellent the UV-shielding effect. The larger the increase in fluorescence intensity, the poorer the UV-shielding effect. In each case, a sample containing neither UV-absorbing agent component (A) nor UV-absorbing agent-solubilizing surfactant component (B) is employed as a reference. The increase in fluorescence intensity of the film coated with the sample is compared with the increase in fluorescence intensity of the film coated with the reference sample.

(Rating for evaluating UV-shielding effect: OO denotes the best rating, and X denotes the worst rating. The same is applied throughout the Examples.)

OO: the ratio of increase in fluorescence intensity of the sample to that of the reference sample containing neither component (A) nor (B) is <50%.

O: the ratio of increase in fluorescence intensity of the sample to that of the reference sample containing neither component (A) nor (B) is ≥50% and <80%.

Δ: the ratio of increase in fluorescence intensity of the sample to that of the reference sample containing neither component (A) nor (B) is ≥80% and <100%.

X: the ratio of increase in fluorescence intensity of the sample to that of the reference sample containing neither component (A) nor (B) is ≥100%.

(2) Assessing Sensation to the Touch (No Overly Dry Sensation)

Each (0.5 g) of the samples (Examples and Comparative Examples) is applied to a tress (2 g) of healthy hair. In the case where the sample is a shampoo, the foamed sample is applied. Thereafter, the tress is washed with a flow of water and then dried. After this treatment, the tress sample is irradiated with artificial sun light by a solar simulator (15 mW/cm$^2$: 290 to 390 nm) for 10 minutes (9 J/cm$^2$). The tress sample is repeatedly (seven times in total) subjected to the set of the treatment and irradiation. The sensation to the touch (no overly dry sensation) of the tress, with comparison to a non-treated tress, was evaluated by 10 expert panelists according to the following criteria:

OO: 8 or more of the 10 expert panelists found no overly dry sensation of the treated tress sample as compared with the non-treated tress sample.

O: 6 or more and less than 8 of the 10 expert panelists found no overly dry sensation of the treated tress sample as compared with the non-treated tress sample.

Δ: 3 or more and less than 6 of the 10 expert panelists found no overly dry sensation of the treated tress sample as compared with the non-treated tress sample.

X: less than 3 of the 10 expert panelists found no overly dry sensation of the treated tress sample as compared with the non-treated tress sample.

2. Examples

Cases in which the Hydrophilic Molecule of Compound (I) is POE Chain (m=0)

(1) Example A-1

Hair-Washing Agent

Hair shampoos were prepared according to the formulations shown in Table 1.

Specifically, citric acid, L-glutamic acid, sodium chloride, sodium benzoate, disodium edetate, and sodium hydroxide were added to purified water at 70° C. for dissolution. Sodium cocoyl methyl taurate, sodium N-lauroyl-N'-carboxymethyl-N'-(2-hydroxyethyl)ethylenediamine, and sodium dodecane-1,2-diolacetic acid ether were added to the solution under stirring. Separately, POE(30) phytosterol or POE hardened castor oil, and 2,4,6-tris[4-(2-ethylhexyloxycarbonyl)anilino]-1,3,5-triazine, 4-tert-butyl-4'-methoxybenzoylmethane, or 2-ethylhexyl p-methoxycinnamate were melted at 80° C., and the thus-prepared mixture was added to the aforementioned solution. Finally, perfume was added to the resultant mixture, followed by cooling to room temperature, to thereby produce a hair shampoo.

The shampoo and the similar products, serving as samples, were evaluated through the aforementioned test methods in terms of UV-shielding effect and sensation to the touch (no overly dry sensation). Table 1 shows the results.

TABLE 1

|  | Ex. A1 | Ex. A2 | Ex. A3 | Comp. Ex. A1 | Comp. Ex. A2 | Comp. Ex. A3 | Comp. Ex. A4 |
|---|---|---|---|---|---|---|---|
| Na cocoyl methyl taurate | 20.0 | 20.0 | 20.0 | 20.0 | 20.0 | 20.0 | 20.0 |
| Na N-lauroyl-N'-carboxymethyl-N'-(2-hydroxyethyl)ethylenediamine | 8.0 | 8.0 | 8.0 | 8.0 | 8.0 | 8.0 | 8.0 |
| Na dodecane-1,2-diol acetic acid ether | 3.0 | 3.0 | 3.0 | 3.0 | 3.0 | 3.0 | 3.0 |
| POE(30) phytosterol | 0.1 | 0.5 | 5.0 | 0.5 | 0.5 | 1.0 | — |
| POE hardened castor oil | — | — | — | — | — | — | 0.5 |
| 2,4,6-Tris[4-(2-ethylhexyloxycarbonyl)anilino]-1,3,5-triazine | 0.01 | 0.1 | 0.1 | — | — | — | 0.1 |
| 4-tert-Butyl-4'-methoxybenzoylmethane | — | — | — | 0.1 | — | 0.1 | — |
| 2-Ethylhexyl p-methoxycinnmanate | — | — | — | — | 0.1 | 0.1 | — |
| Citric acid | 0.01 | 0.01 | 0.01 | 0.01 | 0.01 | 0.01 | 0.01 |
| L-Glutamic acid | 0.2 | 0.2 | 0.2 | 0.2 | 0.2 | 0.2 | 0.2 |
| Sodium chloride | 1.0 | 1.0 | 1.0 | 1.0 | 1.0 | 1.0 | 1.0 |

TABLE 1-continued

|  | Ex. A1 | Ex. A2 | Ex. A3 | Comp. Ex. A1 | Comp. Ex. A2 | Comp. Ex. A3 | Comp. Ex. A4 |
|---|---|---|---|---|---|---|---|
| Sodium benzoate | 0.5 | 0.5 | 0.5 | 0.5 | 0.5 | 0.5 | 0.5 |
| Disodium edetate | q.s. | q.s. | q.s. | q.s. | q.s. | q.s. | q.s. |
| Sodium hydroxide | 0.01 | 0.01 | 0.01 | 0.01 | 0.01 | 0.01 | 0.01 |
| Purified water | bal. | bal. | bal. | bal. | bal. | bal. | bal. |
| Perfume | q.s. | q.s. | q.s. | q.s. | q.s. | q.s. | q.s. |
| UV-shielding effect | ○○ | ○○ | ○○ | Δ | Δ | Δ | Δ |
| Sensation to the touch (no overly dry sensation) | ○○ | ○○ | ○ | Δ | Δ | Δ | Δ |

As is clear from Table 1, the hair cosmetic compositions falling within the scope of the present invention (Examples) exhibited excellent UV-shielding effect and provided favorable sensation to the touch (no overly dry sensation) to the hair in any form of the hair washing cosmetic composition. Regarding Comparative Examples, shampoos containing a UV-absorbing agent other than a triazine UV-absorbing agent (Comparative Examples A1 to A3) and a shampoo containing a surfactant having no phytosteryl skeleton (Comparative Example A4) were tested. These samples of the Comparative Examples did not exhibit sufficient UV-shielding effect or favorable sensation in use (no overly dry sensation).

(2) Example B-1

Hair-Treatment Agent

Hair treatment water products were prepared according to the formulations shown in Tables 2 and 3.

Specifically, ion-exchanged water, ethanol, stearyltrimethylammonium chloride, Na EDTA, and sodium lactate were mixed under stirring with heating at 70° C. Separately, POE hardened castor oil or POE(30) phytosteryl, and vitamin E acetate or 2,4-bis-[{4-(2-ethylhexyloxy)-2-hydroxy}-phenyl]-6-(4-methoxyphenyl)-1,3,5-triazine were melted and mixed at 80° C. The thus-prepared mixture was added to the aforementioned solution and cooled, to thereby produce a hair treatment water product.

The hair treatment water and the similar products, serving as samples, were evaluated through the aforementioned test methods in terms of UV-shielding effect and sensation to the touch (no overly dry sensation). Tables 2 and 3 show the results.

TABLE 2

|  | Comp. Ex. B1 | Comp. Ex. B2 | Ex. B1 |
|---|---|---|---|
| Ion-exchanged water | to 100 | to 100 | to 100 |
| Ethanol | 10.0 | 10.0 | 10.0 |
| Stearyltrimethylammonium chloride | 1.0 | 1.0 | 1.0 |
| Na EDTA | 0.1 | 0.1 | 0.1 |
| Sodium lactate | 0.4 | 0.4 | 0.4 |
| POE hardened castor oil | 0.5 | — | — |
| POE(30) phytosteryl | — | 0.5 | 0.5 |
| Vitamin E acetate | — | 0.1 | — |
| 2,4-Bis-[{4-(2-ethylhexyloxy)-2-hydroxy}-phenyl]-6-(4-methoxyphenyl)-1,3,5-triazine | 0.1 | — | 0.1 |
| UV-shielding effect | X | X | ○○ |
| Sensation to the touch (no overly dry sensation) | X | ○○ | ○○ |

The sample of Comparative Example B1, which contained a surfactant having no phytosteryl skeleton, exhibited low UV-shielding effect and inferior sensation to the touch.

The sample of Comparative Example B2, which contained no UV-absorbing agent having a UV absorption peak in the UVA to UVB regions, exhibited low UV-shielding effect.

In contrast, the sample of Example B1, which contained a surfactant having a phytosteryl skeleton and a UV-absorbing agent having a UV absorption peak in the UVA to UVB regions, exhibited excellent UV-shielding effect and sensation to the touch.

TABLE 3

|  | Ex. B2 | Ex. B3 | Ex. B4 |
|---|---|---|---|
| Ion-exchanged water | to 100 | to 100 | to 100 |
| Ethanol | 10.0 | 10.0 | 10.0 |
| Stearyltrimethylammonium chloride | 1.0 | 1.0 | 1.0 |
| Na EDTA | 0.1 | 0.1 | 0.1 |
| Sodium lactate | 0.4 | 0.4 | 0.4 |
| POE (25) phytosteryl | 5.0 | 0.5 | 0.1 |
| 2,4-Bis-[{4-(2-ethylhexyloxy)-2-hydroxy}-phenyl]-6-(4-methoxyphenyl)-1,3,5-triazine | 0.5 | 0.5 | 0.5 |
| UV-shielding effect | ○○ | ○○ | ○○ |
| Sensation to the touch (no overly dry sensation) | ○○ | ○○ | ○ |

The samples of Examples B2 to B4 contained a surfactant having a phytosteryl skeleton and a UV-absorbing agent having a UV absorption peak in the UVA to UVB regions. By virtue of incorporation of the UV-absorbing-agent-activating agent having a phytosteryl skeleton to the samples, excellent hair damage protecting effect and favorable sensation to the touch were attained. Among the samples, those of Examples B2 and B3, which have a ratio of activating agent having a phytosteryl skeleton to UV-absorbing agent of 1 or more, exhibited very good sensation to the touch and remarkably high solubility of a poorly water-soluble UV-absorbing agent.

Hereinafter, Formulation Examples of the hair cosmetic composition of the present invention in which the hydrophilic molecule of compound (I) is POE chain (m=0) will be described.

Formulation Example A1

Hair Shampoo

| | Ingredients | Amounts (mass %) |
|---|---|---|
| (1) | Na cocoyl methyl taurate | 20.0 |
| (2) | Na N-lauroyl-N'-carboxymethyl-N'-(2-hydroxyethyl)ethylenediamine | 8.0 |
| (3) | Na dodecane-1,2-diolacetic acid ether | 3.0 |
| (4) | POE(30) phytosterol | 2.0 |

-continued

| | Ingredients | Amounts (mass %) |
|---|---|---|
| (5) | 2,4,6-Tris[4-(2-ethylhexyloxycarbonyl) anilino]-1,3,5-triazine | 0.2 |
| (6) | Citric acid | 0.01 |
| (7) | L-Glutamic acid | 0.2 |
| (8) | Sodium chloride | 1.0 |
| (9) | Sodium benzoate | 0.5 |
| (10) | Disodium edetate | q.s. |
| (11) | Sodium hydroxide | 0.01 |
| (12) | Purified water | balance |
| (13) | Perfume | q.s. |

<Production Method>

The same method as employed in producing the hair shampoos shown in Table 1 was employed.

Formulation Example B1

Hair-Styling Cream

| | Ingredients | Amounts (mass %) |
|---|---|---|
| (1) | Volatile isoparaffin | 5.0 |
| (2) | Dimethylpolysiloxane | 2.0 |
| (3) | Ethanol | 5.0 |
| (4) | POE(25) phytosteryl | 0.6 |
| (5) | 2,4-Bis-[{4-(2-ethylhexyloxy)-2-hydroxy}-phenyl]-6-(4-methoxyphenyl)-1,3,5-triazine | 0.1 |
| (6) | Glycerin | 5.0 |
| (7) | Polyoxypropylene decaglyceryl ether | 5.0 |
| (8) | Isostearic acid | 1.0 |
| (9) | POE hardened castor oil | 0.5 |
| (10) | 2-Alkyl-N-carboxymethyl-N-hydroxyethyl imidazoliniumbetaine | 4.0 |
| (11) | Sodium hydroxide | 0.15 |
| (12) | p-Oxybenzoic acid ester | q.s. |
| (13) | Phenoxyethanol | q.s. |
| (14) | 3Na edetate | q.s. |
| (15) | Xanthan gum | 0.5 |
| (16) | Carrageenan | 0.3 |
| (17) | Vinyl acetate-vinylpyrrolidone copolymer | 2.0 |
| (18) | Carboxyvinyl polymer | 0.5 |
| (19) | Purified water | balance |
| (20) | Highly polymerized methylpolysiloxane | 2.0 |

<Production Method>

Ingredients (8) to (10) were uniformly mixed, and the mixture was mixed with ingredients (1), (2), (7), and (20). The resultant mixture was mixed by means of a homomixer, to thereby prepare an emulsion portion. Ingredients (3), (6), and (12) to (19) were mixed to form a solution, and the solution was neutralized with ingredient (11). Subsequently, the emulsion portion was mixed with the neutralized product, and ingredients (4) and (5) dissolved at 80° C. were further mixed therewith, to thereby produce a hair cream of interest.

Formulation Example B2

Foamy Hair Wax

| | Ingredients | Amounts (mass %) |
|---|---|---|
| (1) | Liquid paraffin | 5.0 |
| (2) | Dimethylpolysiloxane | 5.0 |

-continued

| | Ingredients | Amounts (mass %) |
|---|---|---|
| (3) | Glycerin | 5.0 |
| (4) | Propylene glycol | 5.0 |
| (5) | 1,3-Butylene glycol | 5.0 |
| (6) | Butylethylpropanediol | 0.5 |
| (7) | POE(30) phytosteryl | 0.8 |
| (8) | 2,4,6-Tris[4-(2-ethylhexyloxycarbonyl) anilino]-1,3,5-triazine | 0.05 |
| (9) | Jojoba oil | 1.0 |
| (10) | Carnauba wax | 5.0 |
| (11) | POE hardened castor oil | 2.0 |
| (12) | POE behenyl ether | 5.0 |
| (13) | 2-Alkyl-N-carboxymethyl-N-hydroxyethyl imidazoliniumbetaine | 7.0 |
| (14) | Phenoxyethanol | 0.5 |
| (15) | Highly polymerized dimethylpolysiloxane | 0.5 |
| (16) | Purified water | balance |
| (17) | Perfume | q.s. |

Neat liquid/propellant = 90/10 (LPG 0.43 MPa)

<Production Method>

A part of ingredient (16) was dissolved in ingredients (5) and (11), and ingredients (1), (2), (9), (15), and (17) were emulsified in the solution by means of a homomixer, to thereby prepare an emulsion portion. Ingredients (10), (12), (13), and (16) were stirred at 90° C. for dissolution and then quenched, to thereby form transparent wax micro-dispersion. The dispersion and the emulsion portion were mixed under stirring and further mixed with ingredients (3), (4), (6), and (14) heated in advance at 70° C. The resultant mixture was further mixed with ingredients (7) and (8) heated in advance at 80° C., to thereby produce a neat liquid. The neat liquid was charged into a container with liquefied natural gas serving as a propellant, to thereby produce a foamy hair wax.

Formulation Example B3

Hair Spray

| | Ingredients | Amounts (mass %) |
|---|---|---|
| (1) | Ethanol | balance |
| (2) | POE(25) phytosteryl | 1.0 |
| (3) | 2,4-Bis-[{4-(2-ethylhexyloxy)-2-hydroxy}-phenyl]-6-(4-methoxyphenyl)-1,3,5-triazine | 0.5 |
| (4) | N-Methacryloyloxyethyl-N-dimethylammonium α-N-methylcarboxybetaine-alkyl methacrylate copolymer | 5.0 |
| (5) | Vinyl acetate-vinylpyrrolidone copolymer (PVP/VA-S630) | 5.0 |

<Production Method

Ingredients (1) to (5) were mixed, and the mixture was charged into a container with liquefied natural gas serving as a propellant, to thereby produce a hair spray.

<Cases in which the Hydrophilic Molecule of Compound (I) is POE-POP Block Chain (m>0)>

(1) Example A-2

Hair-Washing Agent

Hair conditioners were prepared according to the formulations shown in Table 4.

Specifically, citric acid, sodium citrate, and phenoxyethanol were added to purified water at 70° C. for dissolution. To the solution, behenyltrimethylammonium chloride, cetostearyl alcohol (C16/C18=7:3), hydrogenated rapeseed alcohol, isoprene glycol, highly polymerized methylpolysiloxane, and isostearic acid were added, and the mixture was stirred. Separately, POE(30) POP(10) phytosterol or POE hardened castor oil, and 2,4,6-tris[4-(2-ethylhexyloxycarbonyl)anilino]-1,3,5-triazine, 4-tert-butyl-4'-methoxybenzoylmethane, or 2-ethylhexyl p-methoxycinnamate were melted at 80° C. The thus-prepared melt was added to the aforementioned solution. Finally, perfume was added to the resultant mixture, followed by cooling to room temperature, to thereby produce a hair conditioner.

The hair conditioner and the similar products, serving as samples, were evaluated through the aforementioned test methods in terms of UV-shielding effect and sensation to the touch (no overly dry sensation). Table 4 shows the results.

and 2,4-bis-[{4-(2-ethylhexyloxy)-2-hydroxy}-phenyl]-6-(4-methoxyphenyl)-1,3,5-triazine were melted and mixed at 80° C. The thus-prepared mixture was added to the aforementioned solution and cooled, to thereby produce a hair treatment water.

The hair treatment water and the similar products, serving as samples, were evaluated through the aforementioned test methods in terms of UV-shielding effect and sensation to the touch (no overly dry sensation). Tables 5 and 6 show the results.

TABLE 5

|  | Comp. Ex. B3 | Ex. B5 |
|---|---|---|
| Ion-exchanged water | to 100 | to 100 |
| Ethanol | 10.0 | 10.0 |
| Stearyltrimethylammonium chloride | 1.0 | 1.0 |
| Na EDTA | 0.1 | 0.1 |

TABLE 4

|  | Ex. A4 | Ex. A5 | Ex. A6 | Comp. Ex. A5 | Comp. Ex. A6 | Comp. Ex. A7 | Comp. Ex. A8 |
|---|---|---|---|---|---|---|---|
| Behenyltrimethylammonium chloride | 2.0 | 2.0 | 2.0 | 2.0 | 2.0 | 2.0 | 2.0 |
| Cetostearyl alcohol (C16/C18 = 7:3) | 3.0 | 3.0 | 3.0 | 3.0 | 3.0 | 3.0 | 3.0 |
| Hydrogenated rapeseed alcohol | 3.0 | 3.0 | 3.0 | 3.0 | 3.0 | 3.0 | 3.0 |
| Isoprene glycol | 3.0 | 3.0 | 3.0 | 3.0 | 3.0 | 3.0 | 3.0 |
| POE(30) POP(10) phytosterol | 0.1 | 0.5 | 5.0 | 0.5 | 0.5 | 1.0 | — |
| POE hardened castor oil | — | — | — | — | — | — | 0.5 |
| 2,4,6-Tris[4-(2-ethylhexyloxycarbonyl)anilino]-1,3,5-triazine | 0.01 | 0.1 | 0.1 | — | — | — | 0.1 |
| 4-tert-Butyl-4'-methoxybenzoylmethane | — | — | — | 0.1 | — | 0.1 | — |
| 2-Ethylhexyl p-methoxycinnamate | — | — | — | — | 0.1 | 0.1 | — |
| Citric acid | 0.3 | 0.3 | 0.3 | 0.3 | 0.3 | 0.3 | 0.3 |
| Sodium citrate | 0.08 | 0.08 | 0.08 | 0.08 | 0.08 | 0.08 | 0.08 |
| Phenoxyethanol | 0.3 | 0.3 | 0.3 | 0.3 | 0.3 | 0.3 | 0.3 |
| Highly polymerized methylpolysiloxane | 1.5 | 1.5 | 1.5 | 1.5 | 1.5 | 1.5 | 1.5 |
| Isostearic acid | 0.3 | 0.3 | 0.3 | 0.3 | 0.3 | 0.3 | 0.3 |
| Purified water | bal. | bal. | bal. | bal. | bal. | bal. | bal. |
| Perfume | q.s. | q.s. | q.s. | q.s. | q.s. | q.s. | q.s. |
| UV-shielding effect | ∘∘ | ∘∘ | ∘∘ | Δ | Δ | Δ | Δ |
| Sensation to the touch (no overly dry sensation) | ∘∘ | ∘∘ | ∘ | Δ | Δ | Δ | Δ |

As is clear from Table 4, the hair cosmetic compositions falling within the scope of the invention (Examples) exhibited excellent UV-shielding effect and provided favorable hair sensation to the touch (no overly dry sensation) to the hair in any form of the hair washing cosmetic composition. Regarding Comparative Examples, cosmetic compositions containing an UV-absorbing agent other than a triazine UV-absorbing agent (Comparative Examples A5 to A7) and a cosmetic composition containing a surfactant having no phytosteryl skeleton (Comparative Example A8) were tested. These samples of the Comparative Examples did not exhibit sufficient UV-shielding effect or favorable sensation in use (no overly dry sensation).

(2) Examples B

Hair-Treatment Agents

Hair treatment water products were prepared according to the formulations shown in Tables 5 and 6.

Specifically, ion-exchanged water, ethanol, stearyltrimethylammonium chloride, Na EDTA, and sodium lactate were mixed under stirring with heating at 70° C. Separately, POE hardened castor oil or POE(30) POP(10) phytosteryl, TABLE 5-continued

|  | Comp. Ex. B3 | Ex. B5 |
|---|---|---|
| Sodium lactate | 0.4 | 0.4 |
| POE hardened castor oil | 0.5 | — |
| POE(30) POP(10) phytosteryl | — | 0.5 |
| 2,4-Bis-[{4-(2-ethylhexyloxy)-2-hydroxy}-phenyl]-6-(4-methoxyphenyl)-1,3,5-triazine | 0.1 | 0.1 |
| UV-shielding effect | X | ∘∘ |
| Sensation to the touch (no overly dry sensation) | X | ∘∘ |

The sample of Comparative Example B3, which contained a surfactant having no phytosteryl skeleton, exhibited low UV-shielding effect.

In contrast, the sample of Example B5, which contained a surfactant having a phytosteryl skeleton and a UV-absorbing agent having a UV absorption peak in the UVA to UVB regions, exhibited excellent UV-shielding effect and sensation to the touch.

TABLE 6

| | Ex. B6 | Ex. B7 | Comp. Ex. B4 |
|---|---|---|---|
| Ion-exchanged water | to 100 | to 100 | to 100 |
| Ethanol | 10.0 | 10.0 | 10.0 |
| Stearyltrimethylammonium chloride | 1.0 | 1.0 | 1.0 |
| Na EDTA | 0.1 | 0.1 | 0.1 |
| Sodium lactate | 0.4 | 0.4 | 0.4 |
| POE (25) POP (5) phytosteryl | 0.3 | 0.3 | 0.3 |
| 2,4-Bis-[{4-(2-ethylhexyloxy)-2-hydroxy}-phenyl]-6-(4-methoxyphenyl)-1,3,5-triazine | 0.2 | — | — |
| 2,4,6-Tris-[4-(2-ethylhexyloxycarbonyl) anilino]-1,3,5-triazine | — | 0.2 | — |
| 2-Ethylhexyl p-methoxycinnamate | — | — | 0.2 |
| UV-shielding effect | ⊙⊙ | ⊙⊙ | Δ |
| Sensation to the touch (no overly dry sensation) | ⊙⊙ | ⊙⊙ | ⊙⊙ |

The sample of Comparative Example B4, which contained no UV-absorbing agent having a UV absorption peak in the UVA to UVB regions, exhibited unsatisfactory UV-shielding effect.

In contrast, the samples of Examples B6 and B7, which contained a surfactant having a phytosteryl skeleton, and a UV-absorbing agent having a UV absorption peak in the UVA to UVB regions, said UV-absorbing agent corresponding to a triazine derivative, exhibited remarkably excellent UV-shielding effect and sensation to the touch.

Hereinafter, Formulation Examples of the hair cosmetic composition of the present invention in which the hydrophilic molecule of compound (I) is POE-POP block chain (m>0) will be described.

Formulation Example A2

Hair Conditioner

| | Ingredients | Amounts (mass %) |
|---|---|---|
| (1) | Behenyltrimethylammonium chloride | 2.0 |
| (2) | Cetostearyl alcohol (C16/C18 = 7:3) | 3.0 |
| (3) | Hydrogenated rapeseed alcohol | 3.0 |
| (4) | Isoprene glycol | 3.0 |
| (5) | POE(30) POP(10) phytosterol | 0.5 |
| (6) | 2,4,6-Tris[4-(2-ethylhexyloxycarbonyl) anilino]-1,3,5-triazine | 0.05 |
| (7) | Citric acid | 0.3 |
| (8) | Sodium citrate | 0.08 |
| (9) | Phenoxyethanol | 0.3 |
| (10) | Highly polymerized methylpolysiloxane | 1.5 |
| (11) | Isostearic acid | 0.3 |
| (12) | Purified water | balance |
| (13) | Perfume | q.s. |

<Production Method>

The same method as employed in producing the hair shampoos shown in Table 4 was employed.

Formulation Example B4

Hair-Treatment Product

| | Ingredients | Amounts (mass %) |
|---|---|---|
| (1) | Dimethylpolysiloxane | 15.0 |
| (2) | Poly(oxyethlyene-oxypropylene)-methylpolysiloxane copolymer | 0.1 |
| (3) | POE-methylpolysiloxane copolymer | 0.2 |
| (4) | Highly polymerized dimethylsiloxane-methyl(aminopropyl)siloxane copolymer | 0.5 |
| (5) | Highly polymerized dimethylpolysiloxane | 1.0 |
| (6) | Perfume | q.s. |
| (7) | Ethanol | 10.0 |
| (8) | Propylene glycol | 5.0 |
| (9) | 3Na edetate | q.s. |
| (10) | Xanthan gum | 0.1 |
| (11) | Vinyl acetate-vinylpyrrolidone copolymer | 0.5 |
| (12) | Acrylic acid-alkyl methacrylate copolymer | 0.2 |
| (13) | Carboxyvinyl polymer | 0.4 |
| (14) | Purified water | balance |
| (15) | POE(25) POP(5) phytosteryl | 0.5 |
| (16) | 2,4-Bis-[{4-(2-ethylhexyloxy)-2-hydroxy}-phenyl]-6-(4-methoxyphenyl)-1,3,5-triazine | 0.1 |
| (17) | 2-Amino-2-methyl-1-propanol | q.s. |

<Production Method>

Ingredients (7) to (14) were uniformly mixed, and ingredients (15) and (16) melted and mixed in advance at 80° C. were added to the uniform mixture. Then, an oil phase containing ingredients (1) to (6) was added to the resultant mixture, whereby the product was emulsified. The emulsion was neutralized with ingredient (17), to thereby prepare a hair-treatment product.

Formulation Example B5

Hair Wax

| | Ingredients | Amounts (mass %) |
|---|---|---|
| (1) | Liquid paraffin | 10.0 |
| (2) | Microcrystalline wax | 5.0 |
| (3) | Propylene glycol | 10.0 |
| (4) | POE(30) POP(7) phytosteryl | 0.8 |
| (5) | 2,4-Bis-[{4-(2-ethylhexyloxy)-2-hydroxy}-phenyl]-6-(4-methoxyphenyl)-1,3,5-triazine | 0.1 |
| (6) | Carnauba wax | 5.0 |
| (7) | Isostearic acid | 1.0 |
| (8) | Stearic acid | 2.0 |
| (9) | Pentaerythritol tetra-2-ethylhexanoate | 3.0 |
| (10) | POE glyceryl isostearate | 2.0 |
| (11) | Glyceryl monostearate, self emulsifying | 2.0 |
| (12) | Silicic anhydride | 1.0 |
| (13) | Triethanolamine | 0.3 |
| (14) | Carboxyvinyl polymer | 0.2 |
| (15) | p-Oxybenzoic acid ester | q.s. |
| (16) | 3Na edetate | q.s. |
| (17) | Purified water | balance |

<Production Method>

Ingredients (3) and (14) to (16) were dissolved in ingredient (17), to thereby form an aqueous phase. Ingredients (1), (2), and (6) to (11) were dissolved together at 90° C., to thereby form an oil phase. Ingredient (12) was added to the aqueous phase under stirring, and the mixture was heated to 80° C. The oil phase was added to the heated mixture under stirring, and the resultant mixture was emulsified by means of a homomixer, followed by neutralizing with ingredient (13). Subsequently, ingredients (4) and (5) dissolved in advance at 80° C. were mixed with the neutralized product under stirring, and the mixture was degassed and cooled, to thereby produce a hair wax of interest.

Formulation Example B6

Foamy Styling Composition

| | Ingredients | Amounts (mass %) |
|---|---|---|
| (1) | Volatile isoparaffin | 0.5 |
| (2) | Ethanol | 10.0 |
| (3) | POE(25) POP(5) phytosteryl | 0.5 |
| (4) | 2,4,6-Tris[4-(2-ethylhexyloxycarbonyl)anilino]-1,3,5-triazine | 0.2 |
| (5) | POE hardened castor oil | 0.5 |
| (6) | POE-POP decyl ether | 0.5 |
| (7) | Loquat leaf extract | 0.1 |
| (8) | N-methacryloyloxyethyl-N-dimethylammonium α-N-methylcarboxybetaine-butyl methacrylate copolymer | 5.0 |
| (9) | Purified water | balance |

Neat liquid/propellant = 90/10

<Production Method>

Ingredients (1) to (9) were mixed, and the mixture was charged into a container with liquefied natural gas serving as a propellant, to thereby produce a foamy styling composition.

Formulation Example B7

Hair-Styling Gel

| | Ingredients | Amounts (mass %) |
|---|---|---|
| (1) | Polyoxyethylene-methylpolysiloxane copolymer | 0.5 |
| (2) | Ethanol | 20.0 |
| (3) | Glycerin | 10.0 |
| (4) | Dipropylene glycol | 1.0 |
| (5) | Hydroxypropylmethylcellulose | 0.1 |
| (6) | Carrageenan | 0.1 |
| (7) | Carboxyvinyl polymer | 0.6 |
| (8) | Vinyl acetate-vinylpyrrolidone copolymer | 5.0 |
| (9) | (Methacryloyloxyethylcarboxybetaine/alkyl methacrylate) copolymer | 2.0 |
| (10) | POE(25) POP(5) phytosteryl | 0.5 |
| (11) | 2,4-Bis-[{4-(2-ethylhexyloxy)-2-hydroxy}-phenyl]-6-(4-methoxyphenyl)-1,3,5-triazine | 0.1 |
| (12) | Purified water | balance |
| (13) | Sodium hydroxide | q.s. |

<Production Method>

Ingredients (9) and (10) were dissolved at 80° C., and the solution was added to ingredient (12). Ingredients (1) to (7) were dissolved therein, and the resultant solution was neutralized with ingredient (13). Ingredients (8) and (9) were further added thereto, to thereby prepare a hair-styling gel of interest.

Formulation Example B8

Misty Hair Spray

| | Ingredients | Amounts (mass %) |
|---|---|---|
| (1) | Dimethylpolysiloxane | 1.0 |
| (2) | Ethanol | 5.0 |
| (3) | Stearyl alcohol | 0.1 |
| (4) | Behenyl alcohol | 0.2 |
| (5) | Glycerin | 2.0 |
| (6) | Dipropylene glycol | 1.0 |
| (7) | 1,3-Butylene glycol | 1.0 |
| (8) | Alkyltrimethylammonium chloride (77%) | 0.5 |
| (9) | Polyvinylpyrrolidone N,N-dimethylaminoethyl methacrylic acid copolymer | 2.5 |
| (10) | p-Oxybenzoic acid ester | q.s. |
| (11) | Purified water | balance |
| (12) | Perfume | q.s. |
| (13) | POE(25) POP(5) phytosteryl | 0.5 |
| (14) | 2,4-Bis-[{4-(2-ethylhexyloxy)-2-hydroxy}-phenyl]-6-(4-methoxyphenyl)-1,3,5-triazine | 0.1 |

<Production Method>

Ingredients (1), (3), (4), (6), (7), (8), and (12), and a portion of ingredient (11) were heated at 80° C. for dissolution. The solution was emulsified by means of a high-pressure emulsifier. Ingredients (2), (5), (9), (10), and the remaining portion of ingredient (11) were dissolved in the emulsion, and ingredients (13) and (14) heated in advance at 80° C. was added thereto. The mixture was charged into a mist-forming dispenser, to thereby produce a misty spray of interest.

The invention claimed is:

1. A hair cosmetic composition comprising the following ingredients (1) and (2):
(1) a polyoxy(lower alkylene) addition compound of formula (I):

[F1]

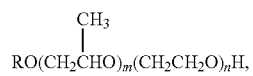

$$RO(CH_2CHO)_m(CH_2CH_2O)_nH,$$ with $CH_3$ substituent wherein R represents a phytosterol residue or a phytostanol residue; m is a number from 0 to 100; and n is a number from 5 to 100, and (2) a UV-absorbing agent having a triazine group.

2. The hair cosmetic composition according to claim 1, wherein the ratio by mass of the polyoxy(lower alkylene) addition compound (I) to the UV-absorbing agent having a triazine group is 1 or higher.

3. The hair cosmetic composition according to claim 1, wherein the phytosterol residue or the phytostanol residue represented by R in the polyoxy(lower alkylene) addition compound (1) is one or more members selected from the group consisting of a sitosterol residue, a campesterol residue, a stigmasterol residue, a brassicasterol residue, an avenasterol residue, an ergosterol residue, a sitostanol residue, a campestanol residue, a stigmastanol residue, a brassicastanol residue, an avenastanol residue, and an ergostanol residue.

4. The hair cosmetic composition according to claim 2, wherein the phytosterol residue or the phytostanol residue represented by R in the polyoxy(lower alkylene) addition compound (I) is one or more members selected from the group consisting of a sitosterol residue, a campesterol residue, a stigmasterol residue, a brassicasterol residue, an avenasterol residue, an ergosterol residue, a sitostanol residue, a campestanol residue, a stigmastanol residue, a brassicastanol residue, an avenastanol residue, and an ergostanol residue.

5. The hair cosmetic composition according to claim 1, which is a water-containing composition.

6. The hair cosmetic composition according to claim 2, which is a water-containing composition.

7. The hair cosmetic composition according to claim 3, which is a water-containing composition.

8. The hair cosmetic composition according to claim 4, which is a water-containing composition.

9. The hair cosmetic composition according to claim 1, which is a hair-washing agent.

10. The hair cosmetic composition according to claim 2, which is a hair-washing agent.

11. The hair cosmetic composition according to claim 3, which is a hair-washing agent.

12. The hair cosmetic composition according to claim 4, which is a hair-washing agent.

13. The hair cosmetic composition according to claim 5, which is a hair-washing agent.

14. The hair cosmetic composition according to claim 6, which is a hair-washing agent.

15. The hair cosmetic composition according to claim 7, which is a hair-washing agent.

16. The hair cosmetic composition according to claim 8, which is a hair-washing agent.

17. The hair cosmetic composition according to claim 1, which is a hair-treatment agent.

18. The hair cosmetic composition according to claim 2, which is a hair-treatment agent.

19. The hair cosmetic composition according to claim 3, which is a hair-treatment agent.

20. The hair cosmetic composition according to claim 4, which is a hair-treatment agent.

21. The hair cosmetic composition according to claim 5, which is a hair-treatment agent.

22. The hair cosmetic composition according to claim 6, which is a hair-treatment agent.

23. The hair cosmetic composition according to claim 7, which is a hair-treatment agent.

24. The hair cosmetic composition according to claim 8, which is a hair-treatment agent.

* * * * *